United States Patent [19]

Müller et al.

[11] Patent Number: 5,196,874
[45] Date of Patent: Mar. 23, 1993

[54] SLIT LAMP APPARATUS WITH PERIPHERAL ILLUMINATION

[75] Inventors: Ortwin Müller, Aalen; Günter Geiss, Königsbronn; Victor Stopar, Oberkochen, all of Fed. Rep. of Germany

[73] Assignee: Carl-Zeiss-Stiftung, Heidenheim, Fed. Rep. of Germany

[21] Appl. No.: 460,916

[22] PCT Filed: Nov. 9, 1988

[86] PCT No.: PCT/EP88/01012
§ 371 Date: Feb. 14, 1990
§ 102(e) Date: Feb. 14, 1990

[87] PCT Pub. No.: WO89/04138
PCT Pub. Date: May 18, 1989

[30] Foreign Application Priority Data

Nov. 10, 1987 [DE] Fed. Rep. of Germany ... 8714962[U]

[51] Int. Cl.⁵ ............................................. A61B 3/02
[52] U.S. Cl. ............................................. 351/221; 351/214; 128/395
[58] Field of Search .............. 351/214, 221; 128/395

[56] References Cited

U.S. PATENT DOCUMENTS 4,102,565  7/1978  Takizawa et al. .
4,883,351  11/1989  Weiss .................................. 351/214
4,991,954  2/1991  Akiyama ............................ 351/214

OTHER PUBLICATIONS

International patent application WO 85/00966 Mar. 1985.
International patent application WO 84/01110 Mar. 1984.

*Primary Examiner*—Rodney B. Bovernick
*Assistant Examiner*—Hung Xuan Dang
*Attorney, Agent, or Firm*—Walter Ottesen

[57] ABSTRACT

A split lamp apparatus includes a peripheral lighting arrangement (3) which can rotate about a vertical axis (5, 6) independently of other parts (1, 2) of the apparatus. In this way, the spot of light from the auxiliary lighting is always located in the focal plane of the slit lamp device (2) and of a stereomicroscope (1). The peripheral lighting arrangement can also be replaced by a laser light source.

5 Claims, 4 Drawing Sheets

SLIT LAMP APPARATUS WITH PERIPHERAL ILLUMINATION

FIELD OF THE INVENTION

The invention relates to a slit lamp apparatus comprising a stereomicroscope, a slit illuminating about a vertical axis, a peripheral illuminating device and an apparatus mechanism coupling the stereomicroscope and the illuminating devices.

BACKGROUND OF THE INVENTION

Slit lamp apparatus which have a peripheral illuminating device in addition to the slit illuminating device are known as so-called photo-slit lamps and are described in the paper "Augenuntersuchung mit der Spaltlampe" published by Carl Zeiss, Oberkochen. With these known photo-slit lamps, it is disadvantageous that the incidence angle of the peripheral illuminating device can only be changed when this illuminating device is pivoted together with the stereomicroscope about the rotational axis of the apparatus mechanism about which the slit illuminating device is also pivotable.

The plane of the slit image and the microscope focal plane contain the virtual extension line of this rotational axis. By means of an instrument base, this plane can be displaced in X, Y, Z direction at the location of the examination in the eye. The mechanical support of this common rotational axis for the slit illuminating device and for the stereomicroscope can be arranged above or below the head of the patient in accordance with the configuration of the slit lamp device.

SUMMARY OF THE INVENTION

The present invention has as an object to equip known slit lamp devices with an additional illuminating device having a direction of incoming radiation which is independent of other apparatus parts and which can be changed independently of the slit illuminating device.

The split lamp apparatus of the invention includes a stereomicroscope, a slit lamp device rotatable about a vertical axis, a peripheral illuminating device and an apparatus mechanism. The apparatus mechanism couples the stereomicroscope and the slit lamp device and a peripheral illuminating device which is also part of the slit lamp apparatus. According to a feature of the invention, the peripheral illuminating device is rotatable about a vertical axis independently of other parts of the slit lamp apparatus.

The advantages achieved with the invention are that the axes of the slit illuminating device and of the peripheral illuminating device can be arranged isocentrically to each other whereby it is assured that the illuminating spot of the additional illumination is always located in the focal plane of the slit illuminating device and of the stereomicroscope. A further advantage of the invention is that in lieu of the peripheral illumination, a laser light source can be arranged. With a laser slit lamp of this kind, it is possible to select the direction of incoming radiation of the laser independently of the viewing direction of the microscope and of the direction of incoming radiation of the slit illumination.

BRIEF DESCRIPTION OF THE DRAWINGS

Embodiments of the invention are illustrated in the drawing and are more carefully described in the following The drawing shows.

DESCRIPTION OF THE PREFERRED EMBODIMENTS OF THE INVENTION

Figure 1:
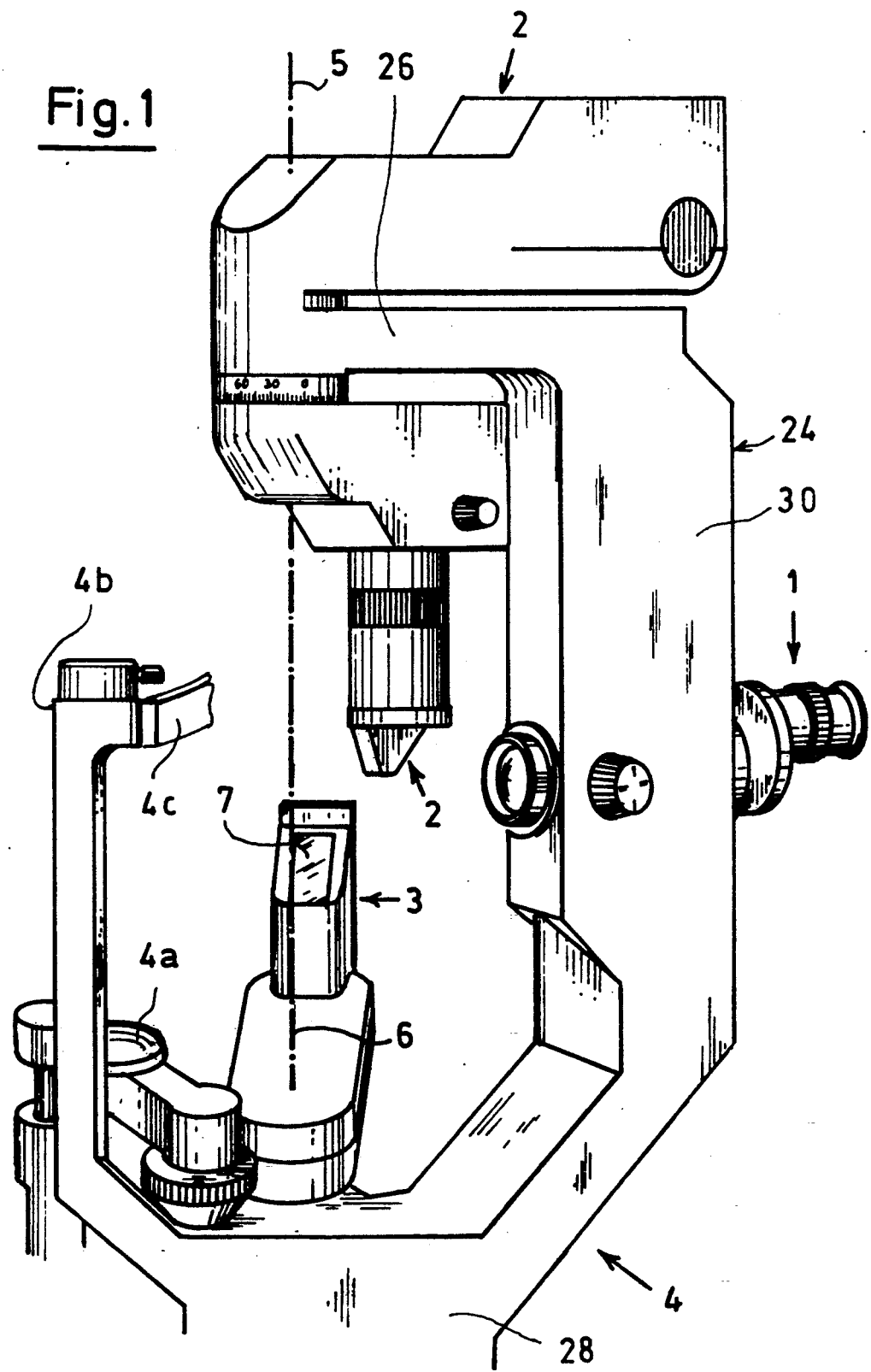
FIG. 1 a perspective illustration of a slit lamp apparatus having an additional peripheral illumination rotatable about a vertical axis.

In the illustration of FIG. 1, a stereomicroscope is identified with reference numeral 1, a slit illuminating device with 2, a peripheral illuminating device with 3 and the apparatus mechanism with 4. The chin support is identified with 4a, the device 4b for holding the head support 4c for the patient. The illuminating device 3 is rotatable about the axis 6 which extends isocentrically to the rotational axis 5. The illuminating device 3 is closed by a window 7 for passing the illuminating radiation.

As shown in FIG. 1, the apparatus 4 includes a frame 24 having a first leg 26, a second leg 28 and a connecting piece 30 interconnecting the legs. The slit illuminating device 2 is rotatably mounted on the first leg 26 at a first position thereon so as to define a vertical first axis 5 of rotation. The stereomicroscope 1 is mounted on the connecting piece 30 of the frame 24. A peripheral illuminating device 3 is rotatably mounted on the second leg 28 of the frame 24 at a second position thereon so as to be rotatable about a vertical second axis 6 independently of the stereomicroscope 1 and the slit illuminating device 2. The first vertical axis 5 is coaxial with the second vertical axis 6 as shown.

Figure 2:
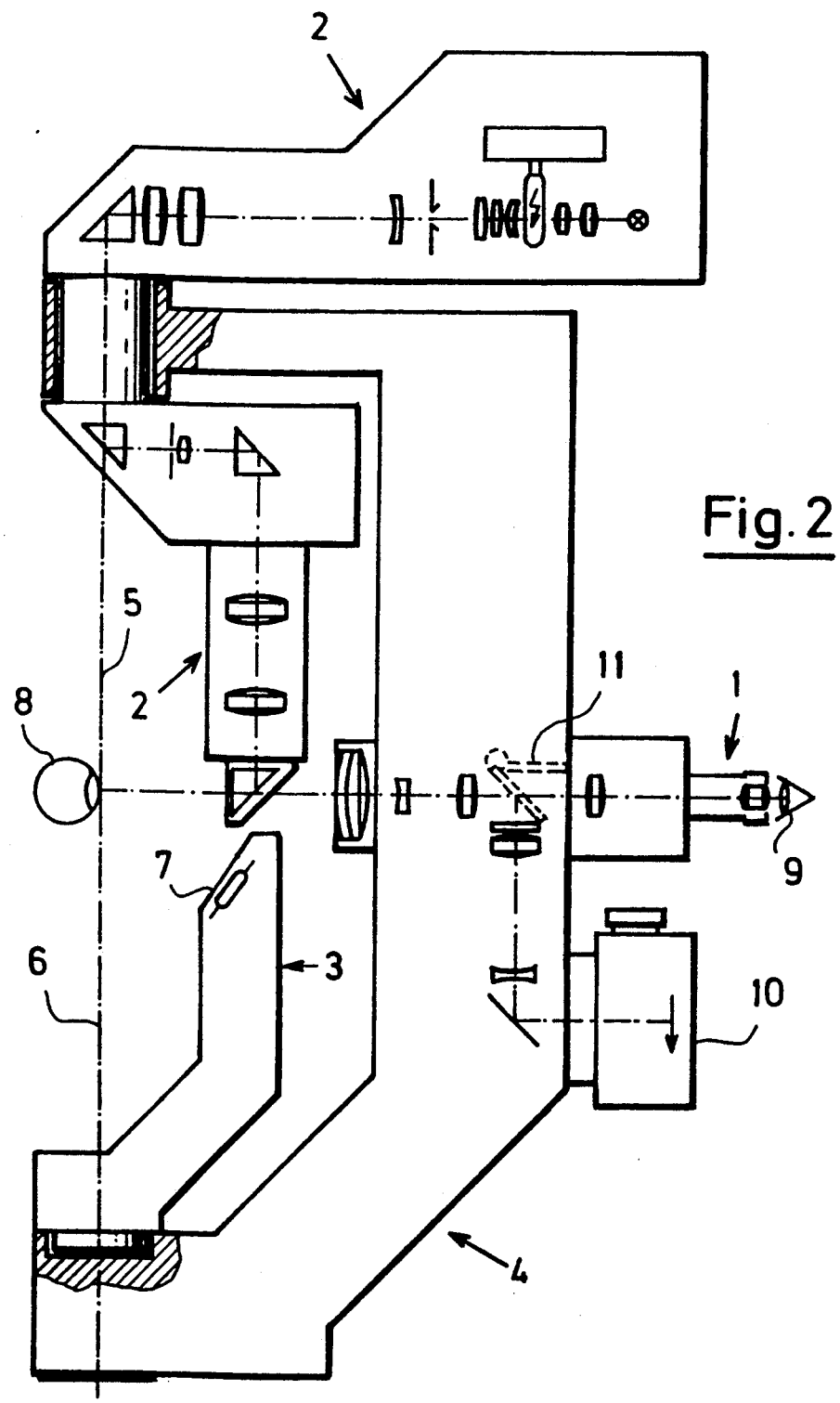
FIG. 2 a section view of the slit lamp device shown in FIG. 1.
Figure 3:
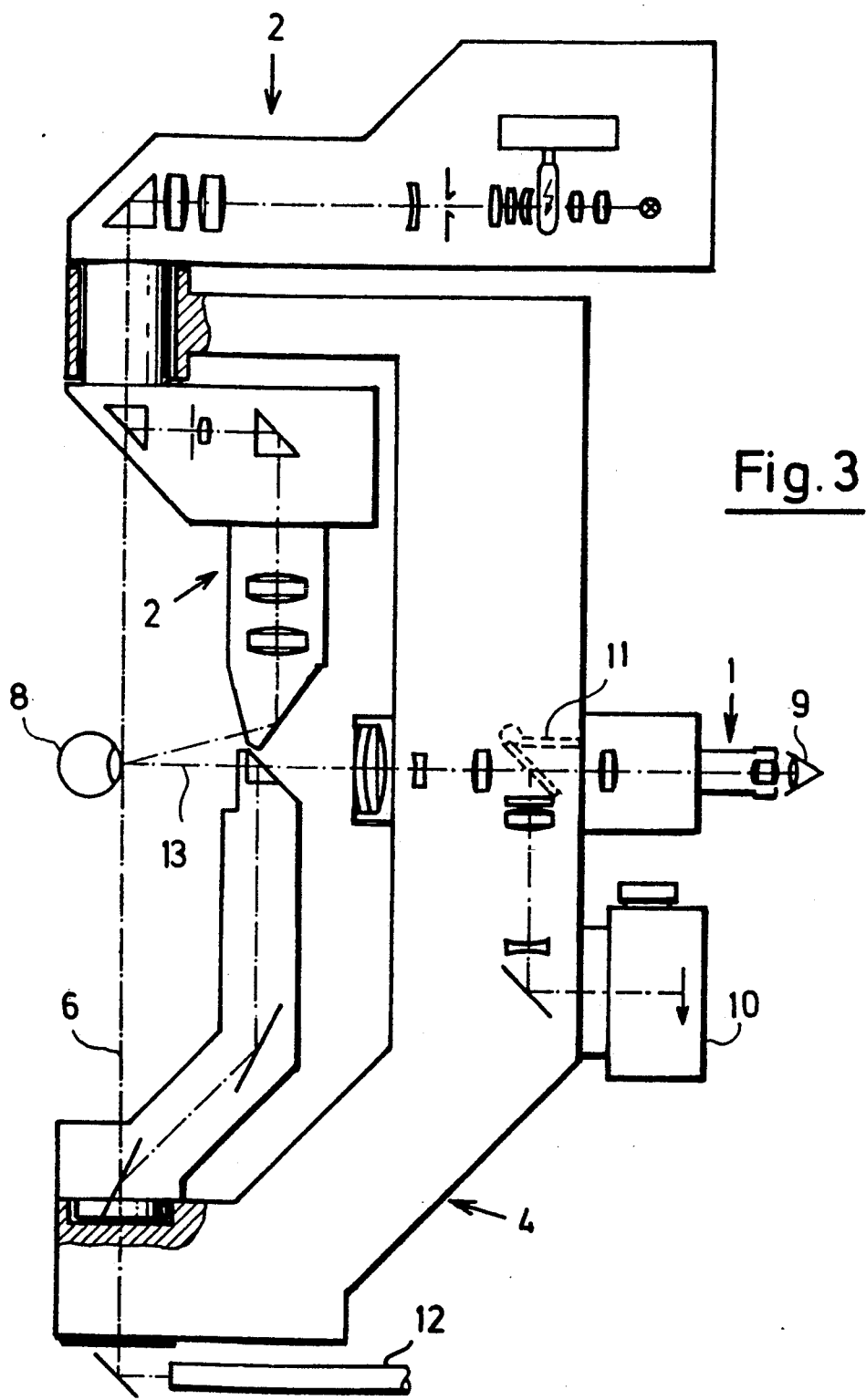
FIG. 3 a section view of a laser slit lamp.

The optical elements for the slit lamp device are shown in the section view of FIG. 2. These elements are not identified individually because they are evident from the known state of the art. The patient eye is identified in this illustration with the reference numeral 8 and the viewing eye with 9. The reference numeral 10 identifies a photographic device for documentation to which the viewing beam can be directed via the hinged mirror 11 when required. In addition, the same reference numerals are used for like apparatus parts as in FIG. 1. The illustration of FIG. 3 shows the same arrangement as FIG. 2 except for the laser light source 12. In this apparatus, the radiation of the light source 12 can be directed to the patient eye 8 for therapeutical purposes in lieu of the peripheral illumination.

Figure 4:
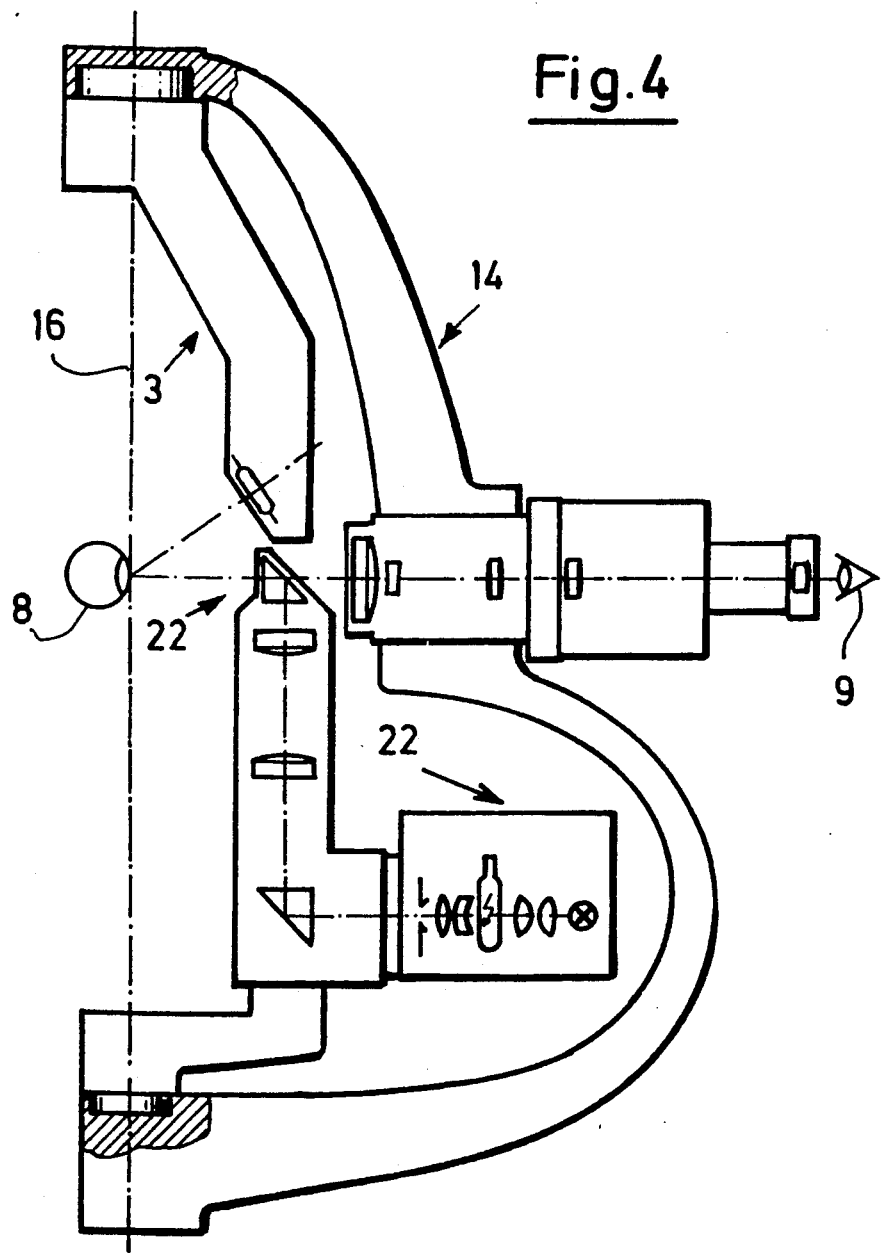
FIG. 4 a section view of a slit lamp apparatus wherein the peripheral illumination is arranged above the eye of the patient.

A slit lamp apparatus having apparatus mechanism 14 is shown in the illustration of FIG. 4 wherein the slit illuminating device 22 is mounted below the patient eye 8 and the peripheral illuminating device 3 is arranged above the patient eye 8. The rotational axis 16 of the peripheral illuminating device extends isocentrically to the rotational axis of the slit lamp illuminating device.

We claim:

1. A slit lamp apparatus comprising:
    a frame;
    a slit illuminating device rotatably mounted on said frame at a first position thereon so as to define a vertical first axis of rotation at said first position;

a stereomicroscope mounted on said frame;

a peripheral illuminating device pivotally mounted on said frame at a second position thereon so as to be pivotable about a vertical second axis at said second position independently of said stereomicroscope and said slit illuminating device, said first and second axes being isocentric.

2. The slit lamp apparatus of claim 1, said stereomicroscope and said slit illuminating device each defining a focal plane; and, said peripheral illuminating device generating an illuminating spot and being mounted at said second position so as to cause said second axis to be isocentric to said first axis whereby said illuminating spot is always located in the focal plane of said slit illuminating device and the focal plane of said stereomicroscope.

3. The slit lamp apparatus of claim 2, said frame having a head support thereon for bracing the head of a patient during an examination; and, said peripheral illuminating device being mounted on said frame so as to cause said peripheral illuminating device to be at an elevation higher than said head support.

4. The slit lamp apparatus of claim 2, said frame having a head support thereon for bracing the head of a patient during an examination; and, said peripheral illuminating device being mounted on said frame so as to cause said peripheral illuminating device to be at an elevation lower than said head support.

5. A slit lamp apparatus comprising:

a frame being side mounted and having first and second legs and a connecting piece interconnecting said legs;

a slit illuminating device rotatably mounted on said first leg at a first position thereon so as to define a vertical first axis of rotation;

a stereomicroscope mounted on said connecting piece of said frame;

a peripheral illuminating device rotatably mounted on said second leg of said frame at a second position thereon so as to be rotatable about a vertical second axis independently of said stereomicroscope and said slit illuminating device; and, said second axis being coaxial with said first axis.

* * * * *